(12) United States Patent
Wampler et al.

(10) Patent No.: US 6,234,772 B1
(45) Date of Patent: May 22, 2001

(54) ROTARY BLOOD PUMP

(75) Inventors: Richard K. Wampler, Granite Bay; David M. Lancisi, Folsom, both of CA (US)

(73) Assignee: Kriton Medical, Inc., Sacramento, CA (US)

( * ) Notice: Subject to any disclaimer, the term of this patent is extended or adjusted under 35 U.S.C. 154(b) by 0 days.

(21) Appl. No.: 09/301,138

(22) Filed: Apr. 28, 1999

(51) Int. Cl.$^7$ .................................................... F04B 17/00
(52) U.S. Cl. ................. 417/423.12; 417/420; 417/423.1; 415/900; 604/151
(58) Field of Search ........................... 417/423.1, 423.12, 417/420, 356, 423.7; 415/900; 604/151

(56) References Cited

U.S. PATENT DOCUMENTS

| | | |
|---|---|---|
| 2,725,266 | 11/1955 | Mendelsohn . |
| 3,487,784 | 1/1970 | Rafferty et al. . |
| 3,493,274 | 2/1970 | Emslie et al. . |
| 3,572,982 | 3/1971 | Kozdon . |
| 3,957,389 | 5/1976 | Rafferty et al. ............................ 415/1 |
| 4,057,369 | 11/1977 | Isenberg et al. . |
| 4,072,370 | 2/1978 | Wasson . |
| 4,135,253 | 1/1979 | Reich et al. . |
| 4,253,798 | 3/1981 | Sugiura . |
| 4,382,199 * | 5/1983 | Isaacson ............................ 417/423.1 |
| 4,382,245 | 5/1983 | Harrigan . |
| 4,507,048 | 3/1985 | Belenger et al. . |
| 4,625,712 | 12/1986 | Wampler . |
| 4,688,998 * | 8/1987 | Olsen et al. ......................... 417/356 |
| 4,704,121 * | 11/1987 | Moise .................................... 415/112 |
| 4,745,345 | 5/1988 | Petersen . |
| 4,763,032 | 8/1988 | Bramm et al. . |
| 4,779,614 | 10/1988 | Moise . |
| 4,789,251 | 12/1988 | McPherson et al. . |
| 4,806,080 | 2/1989 | Mizobuchi et al. . |

(List continued on next page.)

FOREIGN PATENT DOCUMENTS

| | | | |
|---|---|---|---|
| WO 92/06301 * | 4/1992 | (WO) | ..................................... 415/900 |
| WO99/12587 | 3/1999 | (WO) | ..................................... 417/420 |

OTHER PUBLICATIONS

C. Peter Cho et al.; Eddy Current Loss Calculation in the Permanent Magnet of a Large Horse Power Axial–Field Motor; Jun. 14, 1994; Proceedings, Twenty–third Annual Symposium, Incremental Motion Systems & Devices, pp. 245–253.

C. Peter Cho et al.; Cogging Torque Reduction, Axial Force Variation, and Output Torque Effect of a High–Power–Density, Axial Field, Brushless, Permanent Magnet Motor; Jun. 6, 1995; Proceedings, Twenty–fourth Annual Symposium, Incremental Motion Contol Systems & Devices, pp. 297–307.

C. Peter Cho et al.; Feasibiltiy Study of Novel Integrated Electric Motor/Pump for Underwater Applications; Jun. 6, 1995; Proceedings, Twenty–sixth Annual Symposium, Incremental Motion Control Systems & Devices, pp. 309–316.

(List continued on next page.)

Primary Examiner—Charles Freay
Assistant Examiner—Cheryl J. Tyler
(74) Attorney, Agent, or Firm—George H. Gerstman; Seyfarth Shaw

(57) ABSTRACT

An implantable rotary sealless blood pump is provided. The pump can include hydrodynamic, magnetic and hybrid, hydrodynamic/magnetic bearings and combinations thereof. The rotor can include a shaft or the pump can be made shaftless. Close clearances may be maintained between the housing and the rotor by offsetting magnets or offsetting magnets and motor stators.

26 Claims, 14 Drawing Sheets

U.S. PATENT DOCUMENTS

| | | |
|---|---|---|
| 4,846,152 | 7/1989 | Wampler et al. . |
| 4,876,492 | 10/1989 | Lester et al. . |
| 4,880,362 | 11/1989 | Laing et al. . |
| 4,908,012 | 3/1990 | Moise et al. . |
| 4,944,748 | 7/1990 | Bramm et al. . |
| 4,957,504 | 9/1990 | Chardack . |
| 4,976,729 | 12/1990 | Holfert et al. . |
| 4,994,017 | 2/1991 | Yozu . |
| 4,994,078 * | 2/1991 | Jarvik ................................. 415/900 |
| 5,017,103 | 5/1991 | Dahl . |
| 5,049,134 | 9/1991 | Golding et al. ....................... 415/900 |
| 5,055,005 | 10/1991 | Kletschka . |
| 5,078,741 | 1/1992 | Bramm et al. . |
| 5,092,879 | 3/1992 | Jarvik . |
| 5,106,263 | 4/1992 | Irie . |
| 5,112,200 | 5/1992 | Isaacson et al. . |
| 5,112,202 | 5/1992 | Oshima et al. . |
| 5,147,388 | 9/1992 | Yamazaki . |
| 5,149,253 | 9/1992 | Miyamoto et al. . |
| 5,160,246 | 11/1992 | Horiuchi . |
| 5,182,533 | 1/1993 | Ritts . |
| 5,195,877 | 3/1993 | Kletschka . |
| 5,197,865 | 3/1993 | Sevrain et al. . |
| 5,201,642 | 4/1993 | Hinckley . |
| 5,211,546 | 5/1993 | Isaacson et al. . |
| 5,282,849 | 2/1994 | Kolff et al. . |
| 5,290,236 | 3/1994 | Mathewson . |
| 5,302,091 | 4/1994 | Horiuchi . |
| 5,306,295 | 4/1994 | Kolff et al. . |
| 5,316,440 | 5/1994 | Kijima et al. . |
| 5,324,177 | 6/1994 | Golding et al. . |
| 5,342,825 | 8/1994 | Iannello et al. . |
| 5,350,283 | 9/1994 | Nakazeki et al. . |
| 5,370,509 | 12/1994 | Golding et al. . |
| 5,385,581 | 1/1995 | Bramm et al. . |
| 5,392,881 | 2/1995 | Cho et al. . |
| 5,397,349 | 3/1995 | Kolff et al. . |
| 5,397,953 | 3/1995 | Cho . |
| 5,399,074 * | 3/1995 | Nose'et al. ......................... 417/423.1 |
| 5,441,535 | 8/1995 | Takahashi et al. . |
| 5,443,503 | 8/1995 | Yamane . |
| 5,470,208 | 11/1995 | Kletschka . |
| 5,507,629 | 4/1996 | Jarvik . |
| 5,527,159 | 6/1996 | Bozeman, Jr. et al. . |
| 5,569,111 | 10/1996 | Cho et al. . |
| 5,575,630 | 11/1996 | Nakazawa et al. . |
| 5,588,812 | 12/1996 | Taylor et al. . |
| 5,591,017 | 1/1997 | Dwyer . |
| 5,601,418 | 2/1997 | Ohara et al. . |
| 5,607,329 | 3/1997 | Cho et al. . |
| 5,613,935 | 3/1997 | Jarvik . |
| 5,649,811 | 7/1997 | Krol, Jr. et al. . |
| 5,692,882 | 12/1997 | Bozeman, Jr. et al. . |
| 5,695,471 * | 12/1997 | Wampler ........................... 417/423.1 |
| 5,725,357 | 3/1998 | Nakazeki et al. . |
| 5,728,154 | 3/1998 | Crossett et al. . |
| 5,738,503 | 4/1998 | Schmidt-Marloh et al. . |
| 5,746,575 | 5/1998 | Westphal et al. . |
| 5,840,070 * | 11/1998 | Wampler ........................... 417/423.1 |
| 6,074,180 | 6/2000 | Khanwilkar et al. ................ 417/420 |

OTHER PUBLICATIONS

C. Peter Cho et al.; Ongoing Feasibiltiy Study of a Novel Integrated Electric Motor/Pump Concept; Jun. 11, 1996; Proceedings, Twenty–fifth Annual Symposium, Incremental Motion Control Systems & Devices, pp. 51–62.

C. Peter Cho et al.; Energy Losses in Magnetic Lamination Materials of a Novel Integrated Motor/Pump System; Jul. 22, 1997; Proceedings, Twenty–sixth Annual Symposium, Incremental Motion Control Systems & Devices, pp. 325–333.

Tanaka et al., "A New Seal–Less Centrifugal Blood Pump", Japan Journal of Artificial Organs, 14 (3), pp. 1126–1129, (1985).

Nishida et al., "Development of the Terumo Capiox Centrifugal Pump and Its Clinical Application to Open Heart Surgery: A Comparative Study with the Roller Pump", pp. 24–28, (1992).

Kijima et al., "A Straight Path Centrifugal Blood Pump Concept in the Capiox Centrifugal Pump", pp. 32–37, (1993).

Yamane et al. "Fundamental Characteristics of Magnetically Suspended Centrifugal Blood Pump", pp. 130–131 (1994).

Kijima et al., "The Margin of Safety in the Use of a Straight Path Centrifugal Blood Pump", Artificial Organs, 18(9), pp. 680–686, (1994).

"Implantable Artifical Cardiac Blood Pump Prototype Developed", Medical Equipment Journal of Japan, (May 1994).

Yamane et al., "Design of a Centrifugal Blood Pump with Magnetic Suspension", 1 page, Abstract, (Sep. 1994).

Yamane et al., "Design of a Centrifugal Blood Pump with Magnetic Suspension", Artificial Organs, 19(7), pp. 625–630, (1995).

Akamatsu et al., "Recent Studies of the Centrifugal Blood Pump with a Magnetically Suspended Impeller", Artificial Organs, 19(7), pp. 631–634, (1995).

Yamane "Performance Improvements of a Centrifugal Blood Pump with Mono–Pivot Magnetic–Suspension", pp. 538–539, (1996).

Kim et al., "In Vitro Characterization of a Magnetically Suspended Continuous Flow Ventricular Assist Device", 4535 ASAIO Journal, 41 (1995) Jul./Sep. No. 3.

* cited by examiner

ROTARY BLOOD PUMP

FIELD OF THE INVENTION

The invention relates generally to the field of blood pumps. More specifically, the invention pertains to pumps of rotary design, suitable for implantation in humans.

BACKGROUND OF THE INVENTION

Ventricular assist devices ("VAD"), based on sealless rotary blood pumps, do not have drive shafts for the transmission of torque. Transmission of torque can readily be accomplished with the use of magnetic or electromagnetic coupling, but supporting the impeller poses challenges because of the unique properties of blood.

Blood can be used for hydrodynamic support and surface lubrication in sealless rotary pumps. But, the use of blood for lubrication poses many challenges not encountered with conventional lubricants such as oil, graphite, etc. Blood is composed of cellular elements which can be adversely effected or destroyed by mechanical forces and heat. In addition, blood carries large molecules, such as proteins, enzymes and clotting precursors, which can be damaged, denatured or inactivated as a result of heat, shear, material surfaces, or bearing clearances found in rotary blood pumps. Also, the blood can form clots.

Thus, the use of blood for hydrodynamic support and surface lubrication imposes a very narrow range of operating conditions. To avoid cell injury, only very low levels of shear can be produced. To avoid protein denaturation, local heats must not exceed 45 degrees C. To avoid the formation of clots, surfaces must be made of blood compatible materials and rapid exchange of blood within narrow clearances must be ensured.

Accordingly, it is an object of the present invention to provide a rotary blood pump using hydrodynamic bearings, magnet bearings, hybrid hydrodynamic/magnetic bearings or combinations thereof.

It is yet a further object of the present invention to provide a rotary blood pump in which all the internal surfaces are regularly washed by fresh blood to prevent thrombosis from occurring.

It is another object of the present invention to provide a rotary blood pump which does not subject any blood to shear forces, temperatures or materials that would substantially damage blood or adversely react with blood.

It is another object of the present invention to provide a rotary blood pump in which the magnetic and hydrodynamic forces acting on the rotor provide sufficient support to allow elimination of the shaft.

Other objects and advantages will become apparent as the description proceeds.

SUMMARY OF THE INVENTION

In accordance with illustrative embodiments of the present invention, a rotary blood pump includes a pump housing and a rotor comprising an impeller within the housing. In some embodiments, the rotor also includes a shaft. However, it is presently preferred to design the pump in order to eliminate the necessity for a shaft.

The rotor is suspended within the housing by magnetic and hydrodynamic forces or a combination of magnetic and hydrodynamic forces such that under normal conditions there is little or no rubbing contact between the housing and the rotor. To that end, the pump is provided with hydrodynamic bearings, magnetic bearings, hybrid hydrodynamic/magnetic bearings and combinations of these types of bearings.

In certain embodiments of the invention, a rotary blood pump has a housing and a rotor within the housing. The rotor includes an impeller and a shaft. A radial bearing is provided using magnets carried on the shaft and magnets carried on the housing. A hydrodynamic thrust bearing is defined by a gap between the impeller and the housing. A second radial bearing is defined by a gap between the impeller and an inward extension of the housing. The clearance in the gap of the second radial bearing is greater than the clearance in the hydrodynamic thrust bearing in order to provide for greater blood flow in this gap.

In other embodiments of the invention, a portion of one face of the housing and a portion of one face of the impeller have complementary shaped surfaces and are separated by a gap with sufficient clearance that little or no radial hydrodynamic support is provided.

In other embodiments of the invention, the radial magnetic bearing in the area of the pump is eliminated. In certain of these embodiments, a rotary blood pump has a pump housing and a rotor within the housing. The rotor includes an impeller and a shaft. A hydrodynamic thrust bearing is defined by a gap between the impeller and the housing. A hydrodynamic radial bearing in the area of the impeller is defined by a gap between the impeller and an inward extension of the housing.

In further embodiments of the invention, the rotary blood pump is made shaftless. In certain of these embodiments, a rotary blood pump has a pump housing and a rotor comprising an impeller. A hydrodynamic thrust bearing is defined by a gap between the impeller and the housing. A hydrodynamic radial bearing is defined by a gap between the impeller and an inward extension of said housing.

In other embodiments of the invention employing a shaftless rotor, a magnetic radial bearing has one or more magnets carried by the impeller and one or more magnets carried by an inward extension of the housing. A hydrodynamic thrust bearing is defined by a gap between the impeller and the housing.

In certain alternative embodiments of the invention, the clearance of the magnetic radial bearing is reduced so that the bearing provides additional, hydrodynamic support. In other embodiments, the rotary pump includes more than one magnetic radial bearing each comprising one or more magnets carried by the impeller and one or more magnets carried by an inward extension of the housing.

In preferred embodiments of the present invention, the magnets and motor stators can be offset axially, radially or both to provide forces to hold the rotor and its parts in proper relation to the housing, to dampen or prevent eccentric movement of the rotor, or to preload bearings to counteract hydrodynamic pressure. In certain of these preferred embodiments, magnets or motor stators in one part of the pump are offset in such a way to provide opposing forces to magnets or motor stators offset in another part of the pump.

The present invention incorporates new discoveries relating to non-intuitive ways to support the rotor of a blood pump. One especially significant discovery relates to the improvements in the thrust bearings. It has been found that preloading the hydrodynamic thrust bearings by offsetting magnets or motor stators with approximately ½ to ¾ lbs. of force, employing a large bearing surface, and providing for high flow through the bearing achieves substantial benefits. With these improvements, the hydrodynamic thrust bearing provides an unexpected amount of both axial and moment-restoring force to support the rotor in the axial direction and to prevent tilting and eccentric motion of the rotor. The amount of support and stability is so substantial that it is possible to eliminate the forward magnetic bearings in the area of the pump inlet, and the shaft, spindle, spoke and hub of the pump shown in U.S. Pat. No. 5,840,070. Thus, the pump design can be simplified, the manufacturing costs can be reduced, and potentially stagnant areas in the pump can be eliminated.

Through the present invention, substantial improvements and benefits are also provided in the radial or journal bearings in the area of the impeller. The hybrid hydrodynamic/magnetic radial bearings of this invention allow large clearances and provide large blood flow in the journal area without resulting in anticipated increases in blood damage due to shear. It is believed that the magnetic force decreases the load on the bearing and, thus, decreases shear. Any transient loads caused by eccentric movements are counteracted by the spring forces in hydrodynamic thrust bearings and the hydrodynamic and magnetic forces in the hybrid hydrodynamic/magnetic bearings in the journal area. Again, these improvements in support for the rotor further allow for elimination of any forward magnetic bearings and the shaft, spindle, spoke and hub.

Indeed, the support and restoring and stabilizing forces provided by the present invention are so substantial that it is deemed possible to adjust these forces to provide a rotor with motion that has a controlled amount of eccentricity radially, axially or both. If the motion of the rotor is not perfectly circular, further increases in the exchange of blood in the bearings can be achieved.

A more detailed explanation of the invention is provided in the following description and claims, and is illustrated in the accompanying drawings.

DETAILED DESCRIPTION OF ILLUSTRATIVE EMBODIMENTS

The illustrative embodiments of this invention represent presently preferred improvements and advances over the devices described and claimed in U.S. Pat. No. 5,840,070 issued Nov. 24, 1998. Although the entire disclosure of U.S. Pat. No. 5,840,070 is hereby incorporated by reference herein, certain portions of that disclosure will be repeated below in order to aid in understanding the description of the preferred embodiments of the present invention.

Figure 1:
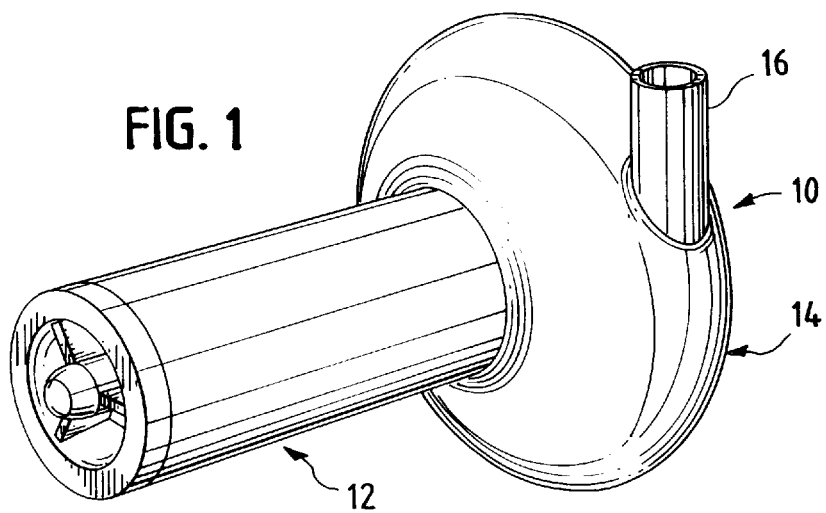
FIG. 1 is a left front perspective of an illustrative embodiment of the blood pump of the present invention.

Referring to FIG. 1 of the drawings, a rotary blood pump 10 includes a housing having an elongated inlet tube 12 and an impeller casing or volute 14. A discharge tube 16 extends through the housing to communicate with the interior of impeller casing 14. Discharge tube 16 has a tangential orientation.

Figure 2:
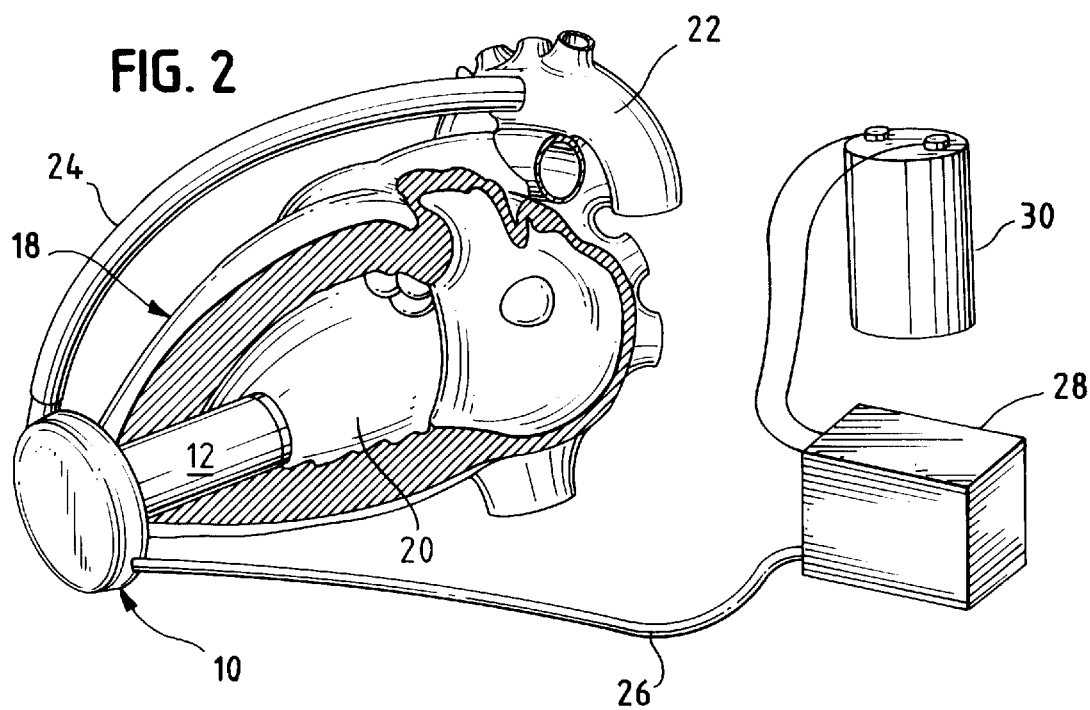
FIG. 2 is a simplified, fragmentary, representation of a human heart, showing the pump implanted within the left ventricle of the heart.

A presently preferred arrangement for the anatomical placement of the pump 10 is shown in FIG. 2. The simplified representation of a heart 18 includes a left ventricle 20 and an aorta 22. The inlet tube 12 serves as the inflow cannula and is placed into the apex of the left ventricle 20. An arterial vascular graft 24 is connected on one end to discharge tube 16 and on the other end of the aorta 22 through an end to side anastomosis. The pump 10 is connected by means of insulated cable 26 to a controller 28 and a power supply 30. It is contemplated that controller 28 and power supply 30 may be worn externally or, alternatively, may be implanted. Rather than using wires, transcutaneous controller and power transmission could be used.

Referring to FIGS. 3, 3A, 4, 5 and 6, pump rotor 32 includes an elongated, cylindrical support shaft or spindle 34 attached to impeller 36. The rotor 32 is mounted for rotation about an longitudinal axis which extends both through shaft 34 and impeller 36.

This embodiment includes a forward magnetic bearing 38. The forward magnetic bearing 38 includes a plurality of rings of axially polarized permanent magnets 40 carried on the inlet tube 12 of the housing and a plurality of rings of axially polarized, disc-shaped, permanent magnets 42 carried on the shaft 34 of the rotor 32.

In the FIGS. 3–6 embodiment, a first motor stator 44 comprising conductive coils or motor windings 46 is located at the rear of casing 14. A ring of backiron 48 is located behind windings 46. First motor stator 44 and backiron 48 are fixed between outside wall of the housing 50 and the inside wall of the housing 52.

Figure 5:
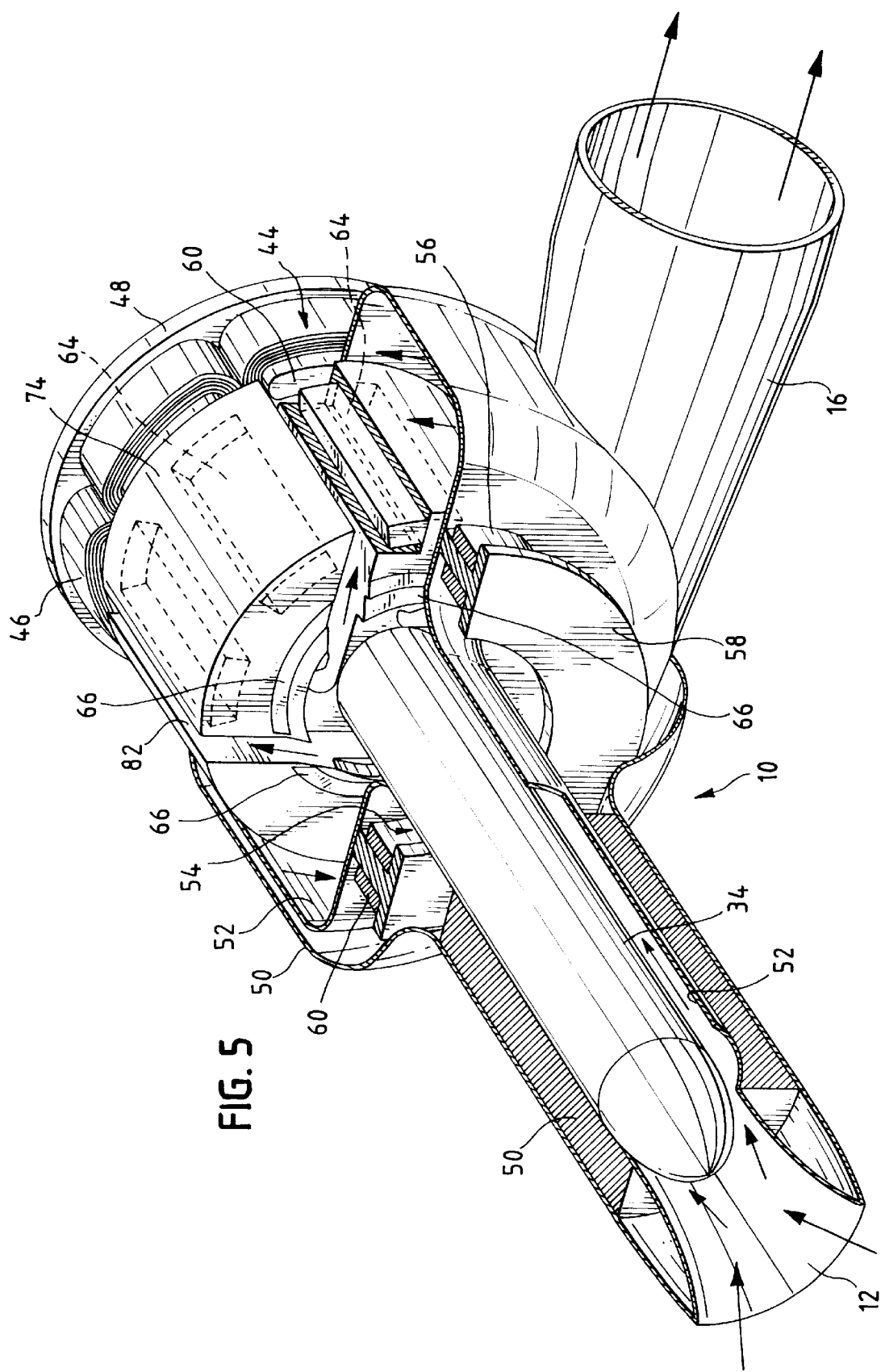
FIG. 5 is a perspective view, partially broken for clarity, of the blood pump of FIG. 3.
Figure 5A:
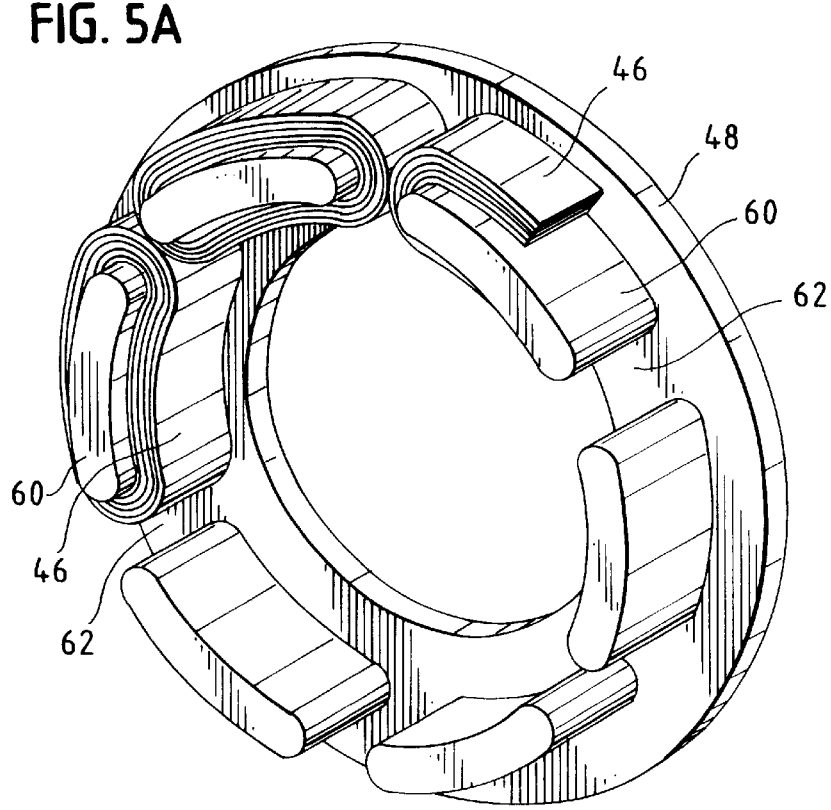
FIG. 5A is a perspective view of a portion of FIG. 5, showing the slotted motor stator.
Figure 5B:
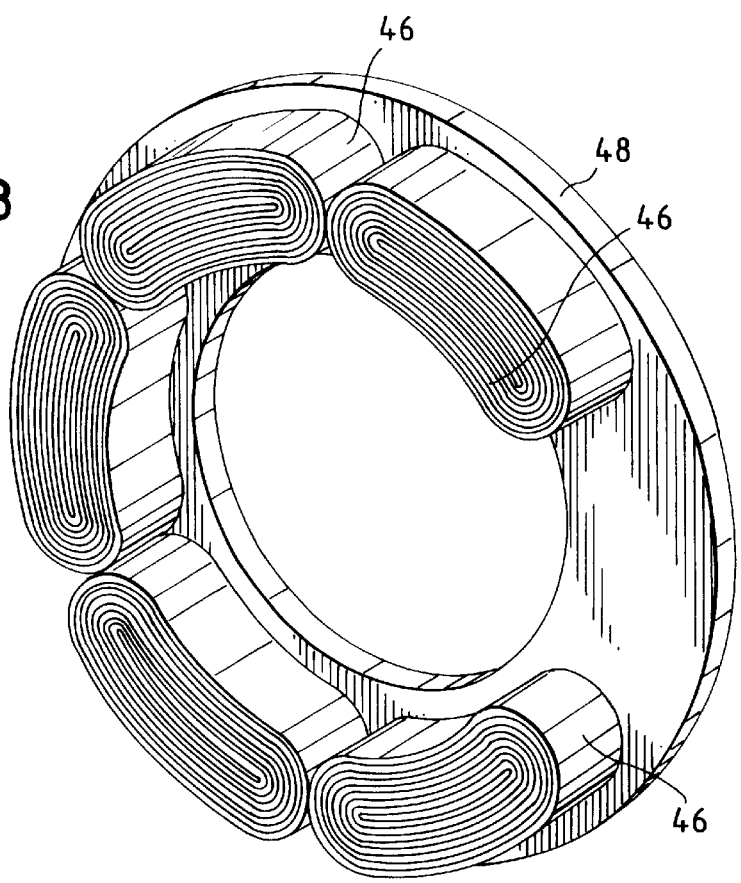
FIG. 5B is a perspective view, similar to FIG. 5A but showing a slotless motor stator.
Figure 6:
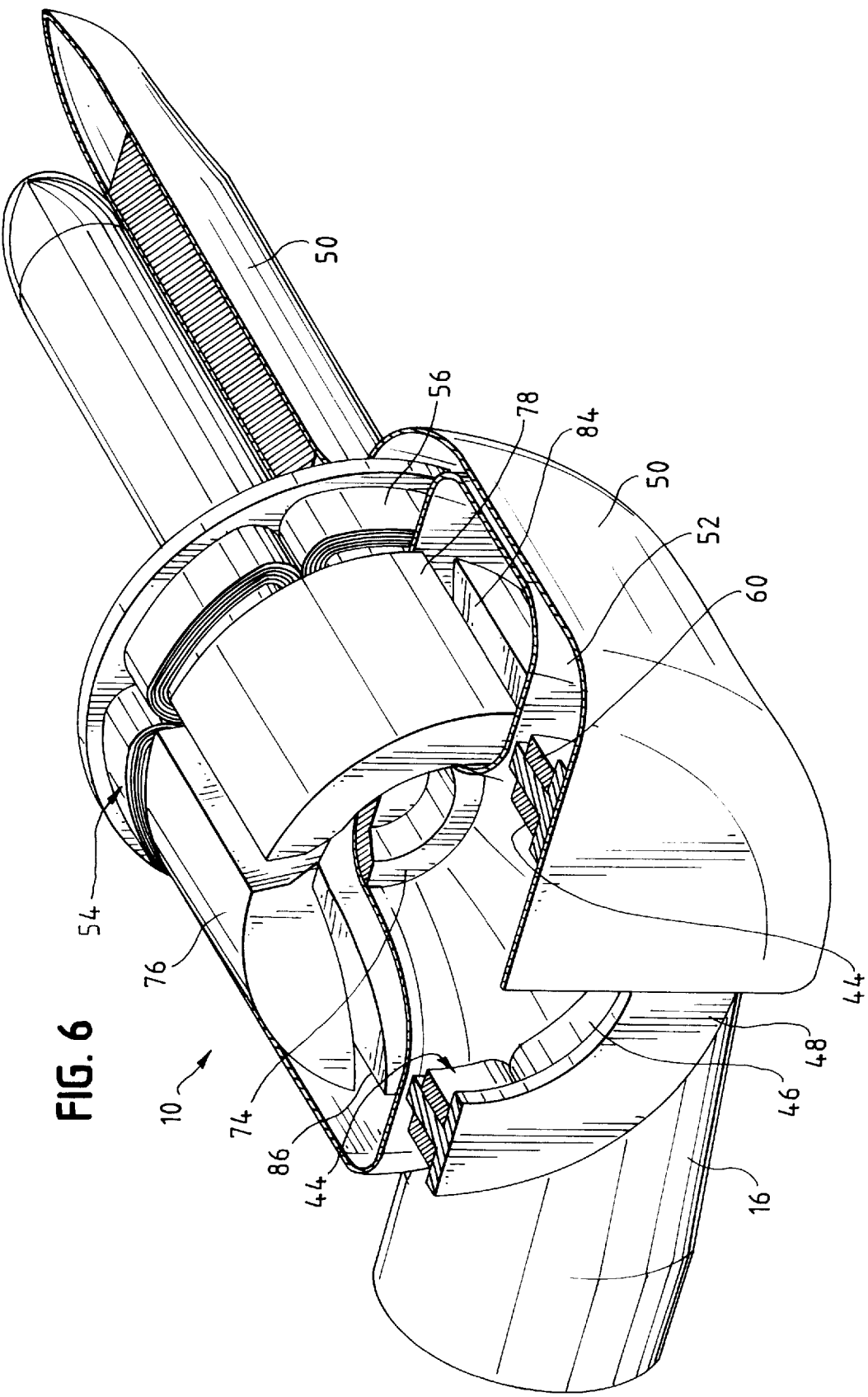
FIG. 6 is another perspective view, partially broken for clarity, of the blood pump of FIG. 3.

A second motor stator 54 comprising windings 56 is positioned on the forward side of casing 14. Windings 56 are fixed to the inside wall of housing 52 of the impeller casing 14 and a ring of backiron 58 is positioned forward of windings 56. As illustrated in FIGS. 5, 5A and 6, backiron 48 and backiron 58 have teeth 60 which extend into the stator windings to form the stator iron. Thus the windings 56 wrap around the teeth 60 in the intervening slots 62 (See FIG. 5A). In the FIG. 5B embodiment, a slotless motor stator is illustrated. In that embodiment, the windings 46 are fixed to the backiron 48 and there are no teeth extending into the stator windings.

It can be seen that the motor stators 44 and 54 are placed on opposite sides of casing 14 such that each is adjacent to the pole faces of the motor rotor magnets 64. Backiron 48 and backiron 58 serve to complete a magnetic circuit. The windings 46 and 56 of the stators 44, 54 can be in series or each stator 44, 54 can be commutated independent of the other. There are several advantages to this approach.

First, as long as the pole faces of the motor rotor magnets are centered between the faces of the motor stators, the net axial force will be relatively low.

Second, the radial restoring force which results from the attractive force of the motor rotor magnets to the motor stators will be nearly twice as large as the restoring force with only one stator. The total volume and weight of the motor will be smaller than a single stator design.

Third, the dual stator design is adapted to provide system redundancy for a fail safe mode, since each stator can be made to operate independently of the other in the case of a system failure.

Figure 3:
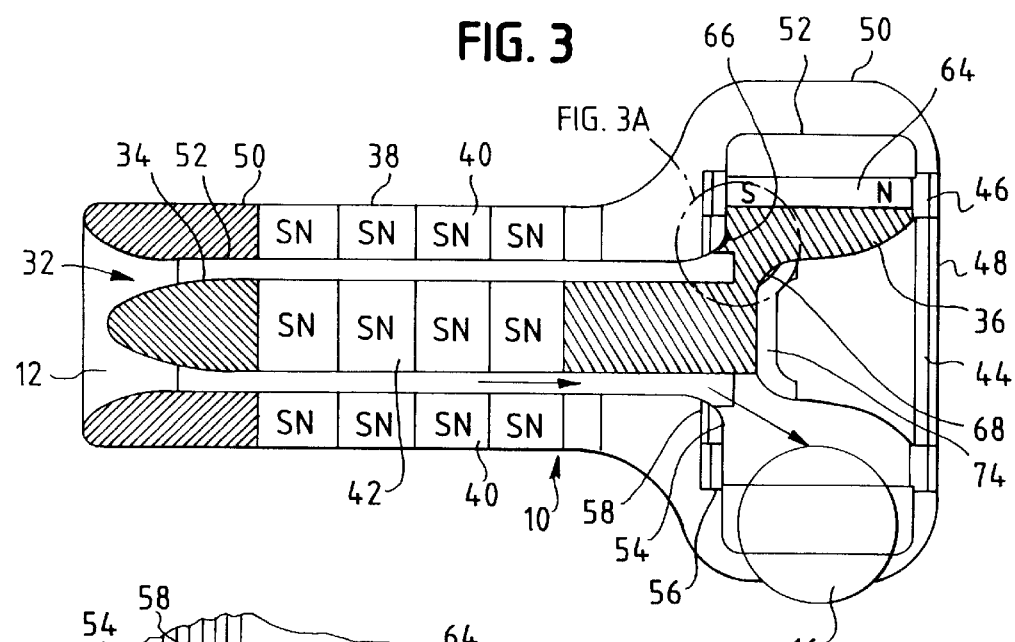
FIG. 3 is a longitudinal, cross-sectional view of a simplified, schematic representation of an illustrative embodiment of the pump.
Figure 3A:
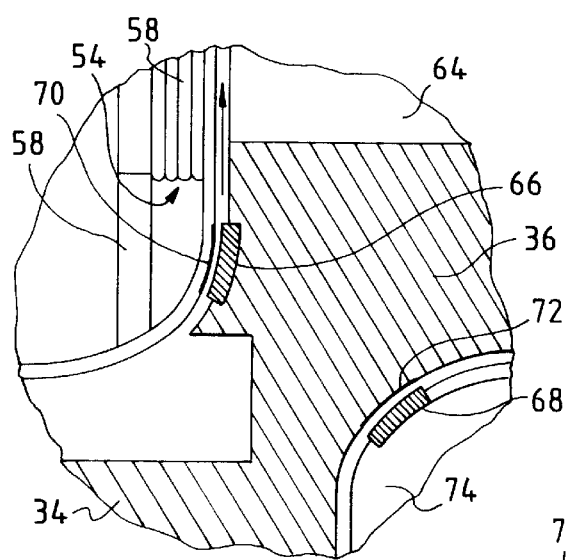
FIG. 3A is an enlarged view of the circled portion 3A from FIG. 3.

Fourth, hydrodynamic bearings can be located on the surface of the impeller to constrain axial motion and to provide radial support in the case of eccentric motion or shock on the device. Referring to FIGS. 3 and 3a in particular, hydrodynamic bearings in the form of raised pads 66, 68 and contact surfaces 70 and 72 are illustrated. Such hydrodynamic bearings are symmetrically located about the impeller as illustrated in FIG. 5 in which raised pads 66 are shown.

The raised pads could be rectangularly-shaped or wedge-shaped and are preferably formed of hardened or wear resistant materials such as ceramics, diamond coatings or titanium nitride. Alternatively, the raised pads may be formed of a different material having an alumina or other ceramic coating or insert.

The raised pads are carried by either the impeller or the casing, or an attachment to the casing. In the FIGS. 3 and 3a embodiment, the raised pads 66 are carried by the impeller and the raised pads 68 are carried by a cup-shaped member 74 that is fastened to the casing in the journal area of the pump. Cup-shaped member 74 is utilized as a reinforcement for the casing which would not be structurally stable enough to carry the raised pads itself.

The hydrodynamic bearings are formed by a raised pad spaced from a contact surface by the blood gap. Although at rest there may be contact between the impeller and the casing, once rotation begins each hydrodynamic bearing is structured so that, during relative movement between the raised pad and the contact surface, the hydrodynamic action of the fluid film produces increased pressure within the bearing gap which forces the raised pad and the contact surface apart.

Depending upon the location of the hydrodynamic bearings, they can aid in axial support, radial support or both axial and radial support. For example, if the bearings are perpendicular to the rotational axis, they aid primarily in axial support but if they are at an angle with respect to the rotational axis, they aid in both radial and axial support. In the embodiment of FIGS. 3–6, the hydrodynamic bearings are positioned outside the axis of rotation, as illustrated.

Figure 4:
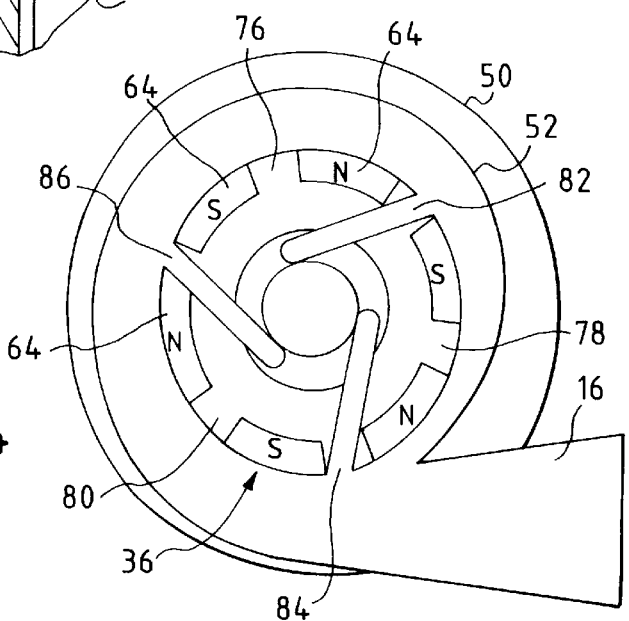
FIG. 4 is a cross-sectional end view of the FIG. 3 pump with the end of the housing removed for clarity.

Referring to FIG. 4 an impeller 36 is shown therein having a number of blade sectors 76, 78 and 80. Blade sectors 76 and 78 are separated by slot 82; blade sectors 78 and 80 are separated by slot 84; and blade sectors 80 and 76 are separated by slot 86. By utilizing blade sectors 76, 78 and 80 that are relatively thick in the axial direction, narrow and deep impeller blood flow paths are formed by slots 82, 84 and 86 between the adjacent edges of the blade sectors. By increasing the thickness of the blade sectors and narrowing the blood passageway, the ratio between the area of working surface of the blades and the volume of the passageway is increased. Also the average distance of the liquid in the passageway from the working surface of the blades is decreased. Both of these beneficial results allow a small pump for blood which has less blades for potentially damaging blood, yet the small pump maintains acceptable efficiency. Another benefit of the thick impeller is the ability to utilize magnetic pieces 64 that are inserted in a manner enabling the stators to be on opposite sides of the impeller.

Figure 7:
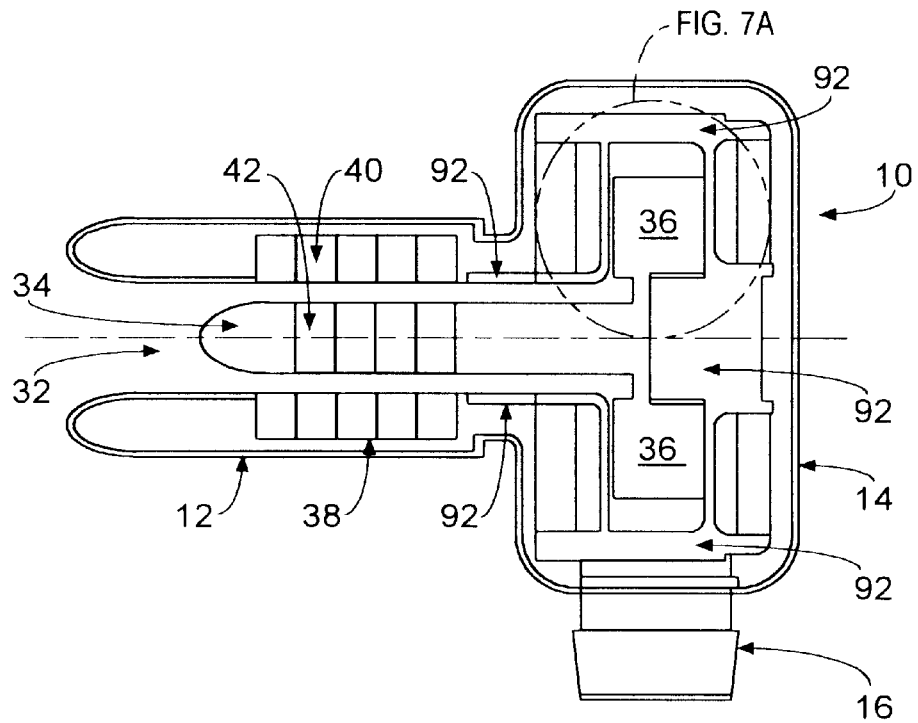
FIG. 7 is a longitudinal, cross-sectional view of another embodiment of the pump.
Figure 7A:
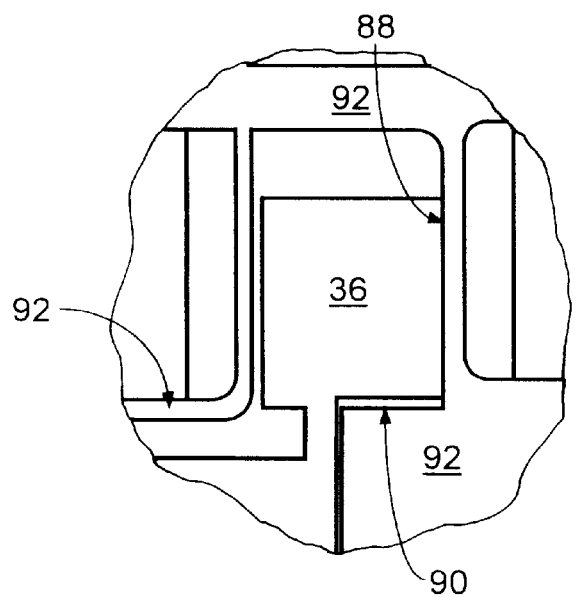
FIG. 7A is an enlarged view of the circled portion 7A of FIG. 7.

Another embodiment of the blood pump 10 is shown in FIGS. 7 and 7A. This embodiment includes forward magnetic bearing 38 including a plurality of magnets 40 carried on the inlet tube 12 of the housing and a plurality of magnets 42 carried on the shaft 34. As best shown in FIG. 7A, this embodiment includes at least one hydrodynamic thrust bearing defined by a gap 88 between the impeller 36 and the housing. This embodiment also includes at least one radial bearing defined by a gap 90 between the impeller 36 and an inward extension of the housing in the journal area. The minimum clearance in gap 88 is about 0.0005–0.0015 inches and in gap 90 is about 0.006–0.020 inches.

The housing includes a hard, smooth, ceramic surface 92 in the area of the impeller 36 which extends forward into the area of the shaft 34. The ceramic surface 92 prevents contact between blood and the metal parts mounted on the housing such as, for example, magnets, motor coils and backirons and protects the housing in case of contact between the rotor and the housing. In certain embodiments, it may be preferable to make the entire housing out of ceramic or to make the entire outer and inner surfaces of the housing out of ceramic.

Figure 8:
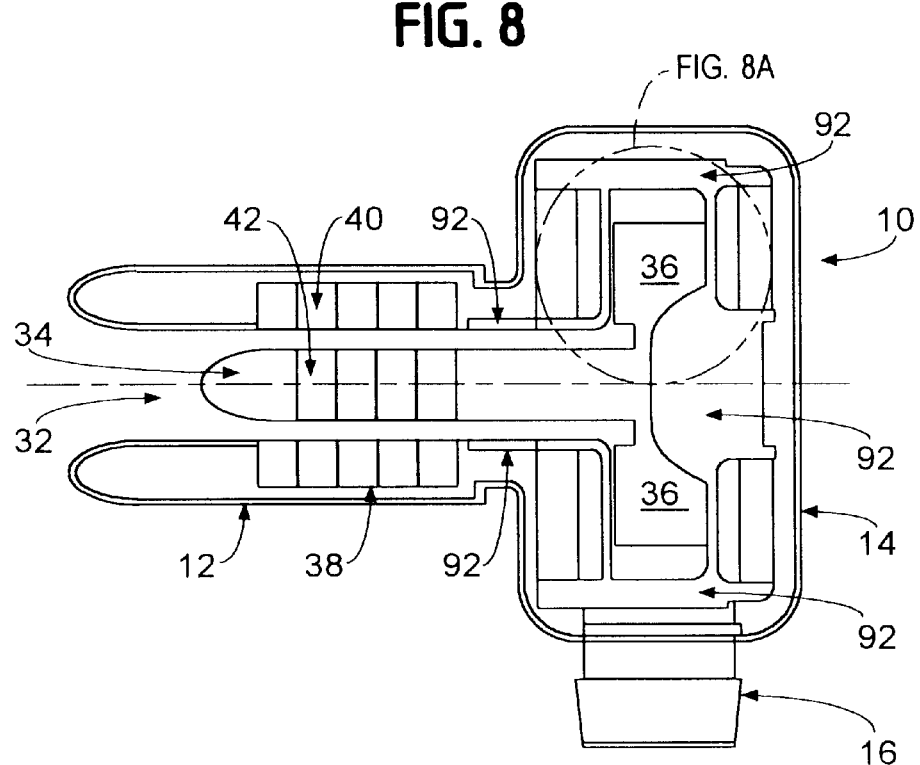
FIG. 8 is a longitudinal, cross-sectional view of another embodiment of the pump.
Figure 8A:
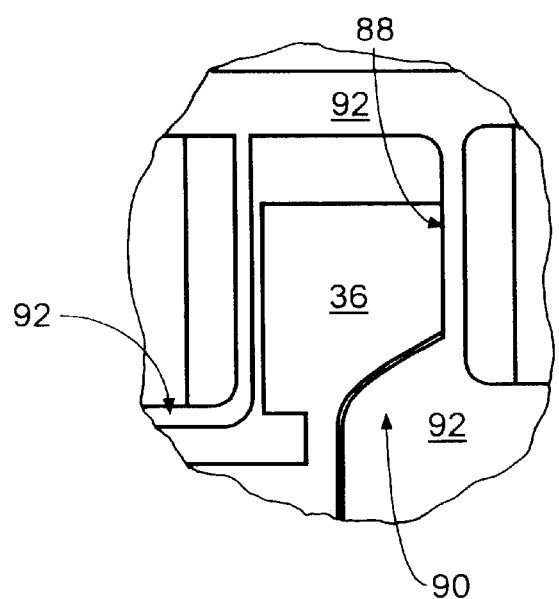
FIG. 8A is an enlarged view of the circled portion 8A of FIG. 8.

Another embodiment of the blood pump 10 is shown in FIGS. 8 and 8A. This embodiment differs from the embodiment of FIGS. 7 and 7A in that the gap 94 between complementary-shaped surfaces on a rear portion of the inside face of the housing and a portion of the rear face of the impeller 36 in the journal area has sufficient clearance such that this gap does not under normal operating conditions provide radial, hydrodynamic support. The minimum clearance in gap 94 is at least about 0.010 inch.

Figure 9:
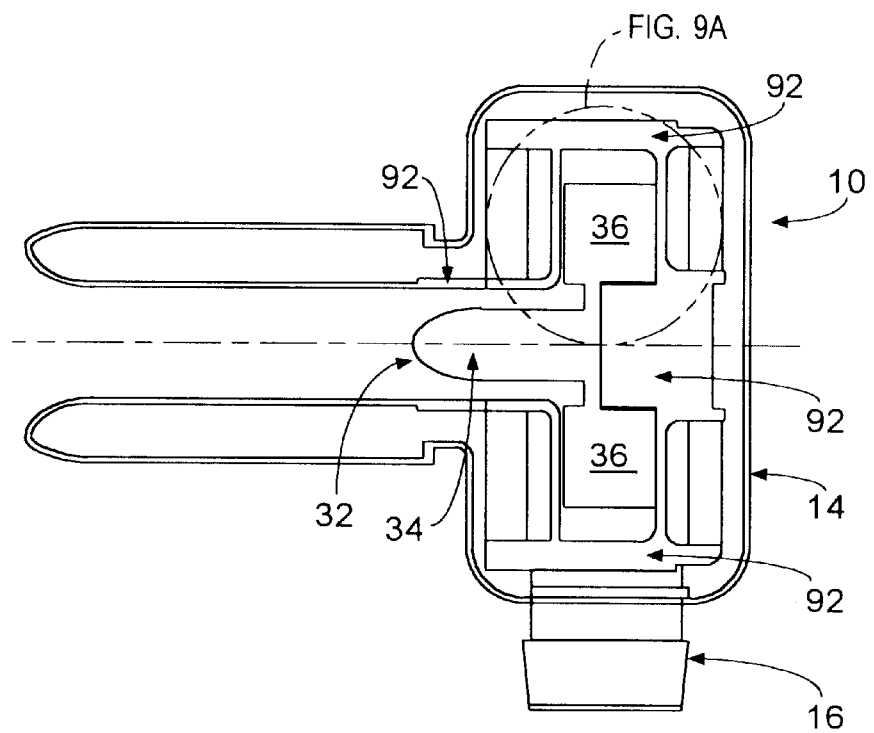
FIG. 9 is a longitudinal, cross-sectional view of another embodiment of the pump.
Figure 9A:
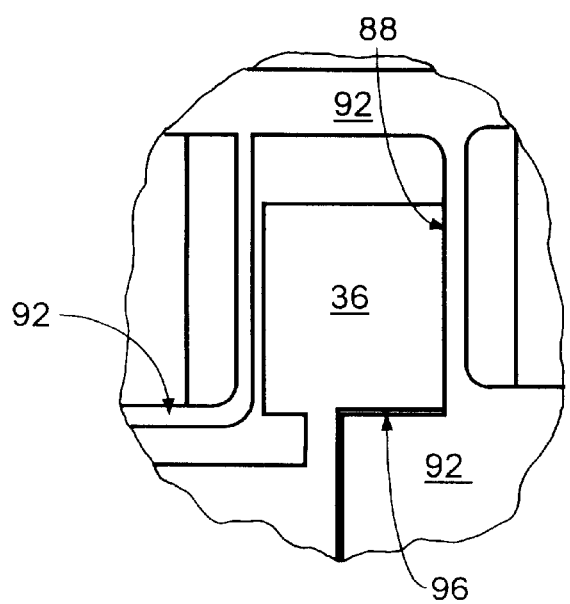
FIG. 9A is an enlarged view of the circled portion 9A of FIG. 9.

Another embodiment of the blood pump 10 is shown in FIGS. 9 and 9A. In this embodiment, the shaft 34 of the rotor 32 is shortened and there are no forward radial bearings or related magnets. In this embodiment, a hydrodynamic thrust bearing is defined by a gap 88 between the impeller and the housing. A hydrodynamic, radial bearing is defined by a gap 96 between the impeller 36 and an inward extension of the housing in the journal area. The minimum clearances in the gap 88 and in the gap 96 are about 0.0005–0.0015 inches.

Figure 10:
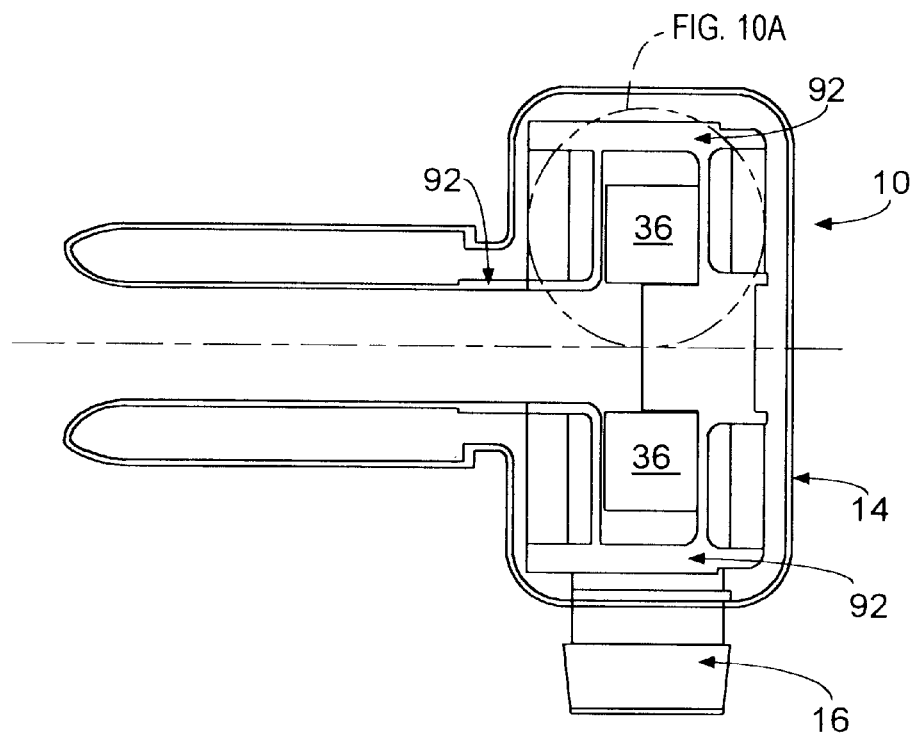
FIG. 10 is a longitudinal, cross-sectional view of another embodiment of the pump.
Figure 10A:
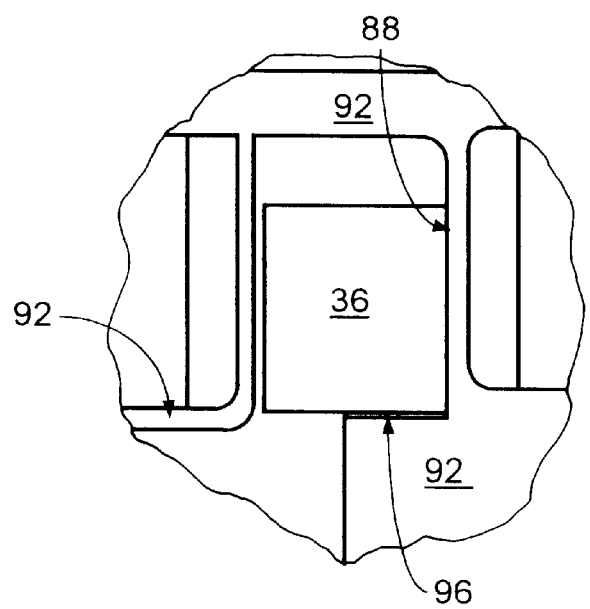
FIG. 10A is an enlarged view of the circled portion 10A of FIG. 10.

Another embodiment of the blood pump 10 is shown in FIGS. 10 and 10A. In this embodiment, the shaft of the rotor is eliminated. Therefore, the rotor comprising the impeller 36 is a ring. As in the embodiment of FIGS. 9 and 9A, a hydrodynamic, thrust bearing is defined by a gap 88 between the impeller and the housing and a hydrodynamic, radial bearing is defined by a gap 96 between the impeller 36 and an inward extension of the housing in the journal area. The minimum clearances in gaps 88 and 96 are about 0.0005–0.0015 inches.

Figure 11:
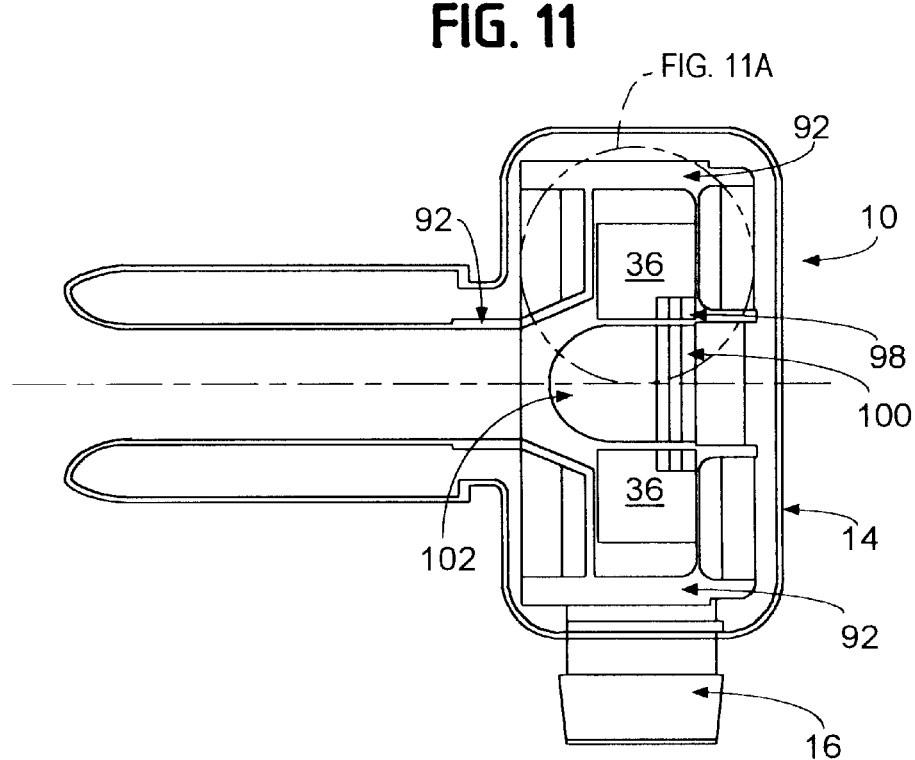
FIG. 11 is a longitudinal, cross-sectional view of another embodiment of the pump.
Figure 11A:
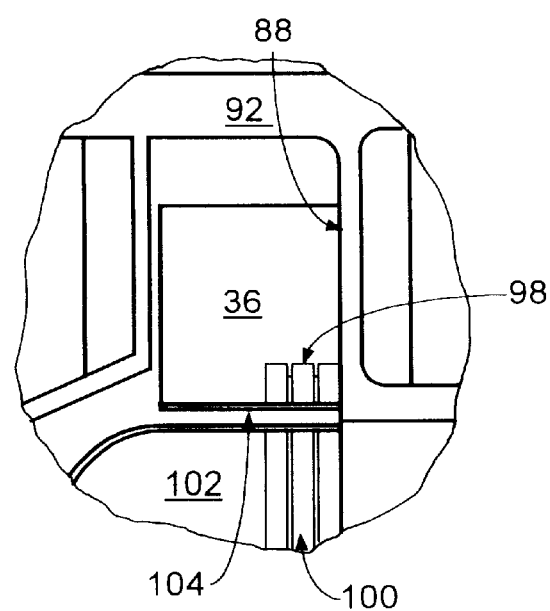
FIG. 11A is an enlarged view of the circled portion 11A of FIG. 11.

Another embodiment of the blood pump 10 is shown in FIGS. 11 and 11A. In this embodiment, the rotor is shaftless and the rotor comprises a ring-shaped impeller 36. A magnetic radial bearing comprises one or more magnets 98 carried on the impeller 36 and one or more magnets 100 carried on an inward extension 102 of the housing in the journal area. In FIG. 11, the magnetic radial bearing and the magnets 98 and the magnets 100 are shown adjacent the rear end of the impeller 36. This magnetic bearing could, of course, be placed in the center of the impeller, adjacent the forward end of the impeller or elsewhere as long as radial support for the rotor is provided. The gap 104 between the impeller 36 and the inward extension 102 of the housing has a minimum clearance of 0.003 inch and a preferred clearance of 0.006–0.020 inches. A hydrodynamic thrust bearing is defined by the gap 88 with a clearance of 0.0005–0.0015 inches.

One presently contemplated alternative to the embodiment shown in FIGS. 11 and 11A has a gap with a clearance of 0.002–0.008 inches between the impeller 36 and the inward extension 102 of the housing in the location of gap 104. With this clearance, the gap would define a hydrodynamic, magnetic radial bearing in the journal area.

Figure 12:
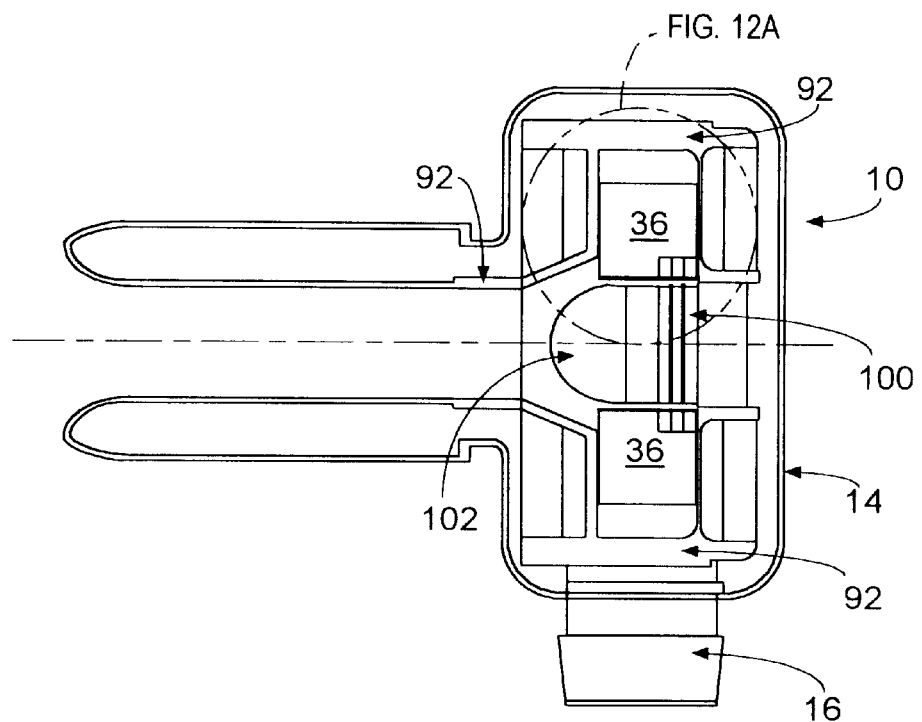
FIG. 12 is a longitudinal, cross-sectional view of another embodiment of the pump.
Figure 12A:
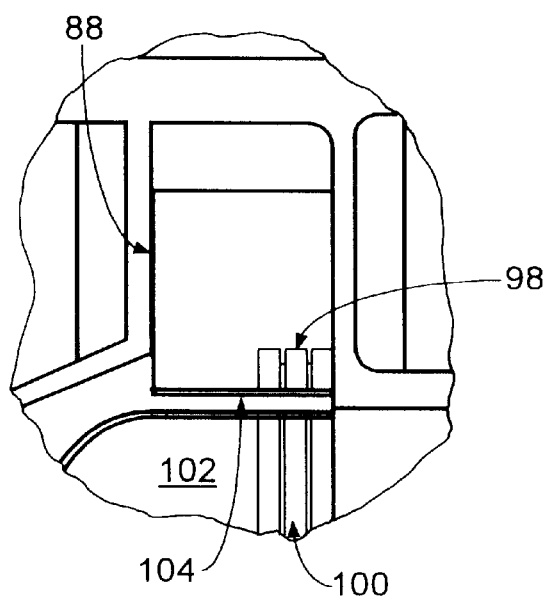
FIG. 12A is an enlarged view of the circled portion 12A of FIG. 12.

Another presently contemplated alternative to the embodiment shown in FIGS. 11 and 11A is shown in FIGS. 12 and 12A. In this embodiment, the hydrodynamic bearing defined by the gap 88 is adjacent the front side (i.e., the direction of the pump inlet) of the impeller 36. It is believed that placement of the hydrodynamic bearing in this forward position could also be beneficial in the other embodiments shown herein.

Figure 13:
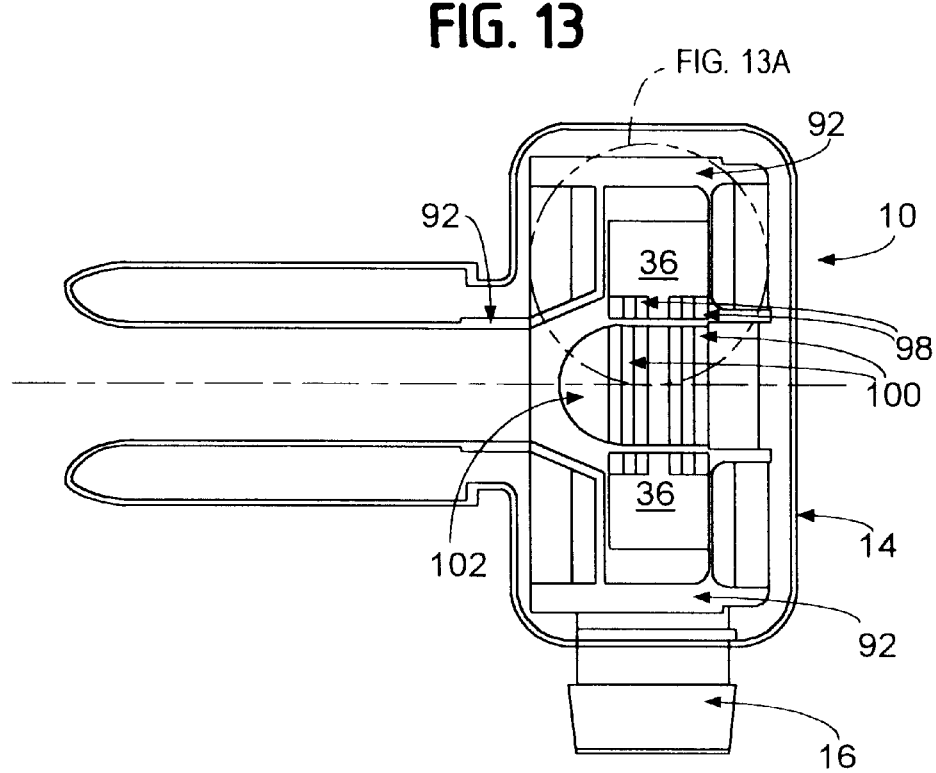
FIG. 13 is a longitudinal, cross-sectional view of another embodiment of the pump.
Figure 13A:
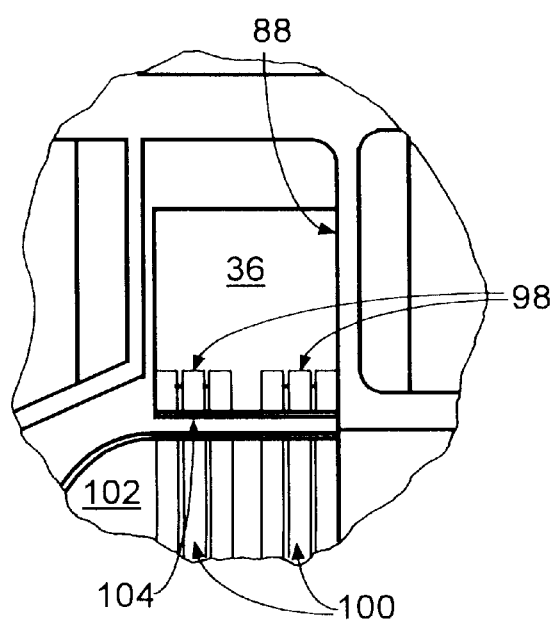
FIG. 13A is an enlarged view of the circled portion 13A of FIG. 13.

Another embodiment of the blood pump 10 is shown in FIGS. 13 and 13A. This embodiment is shaftless and there are two magnetic radial bearings comprising two sets of magnets 98 carried on the impeller 36 and two sets of magnets 100 carried on an inward extension of the housing in the journal area. The gap 104 between the impeller 36 and the inward extension 102 of the housing has a minimum clearance of 0.003 inch. A hydrodynamic thrust bearing is defined by a gap 88 with a clearance of 0.0005–0.0015 inches.

It should be understood that the clearances for the gaps set forth in this application are approximate clearances anticipated during normal operation of the pumps of the present invention and therefore represent minimum film thicknesses. When a pump is not running, is starting up, and other abnormal conditions, the clearances in the gaps will be different. When the magnets or motor stators are offset to provide a preload force on a bearing, there may be zero clearance between parts of the rotor and the housing when the pump is not running.

Figure 14:
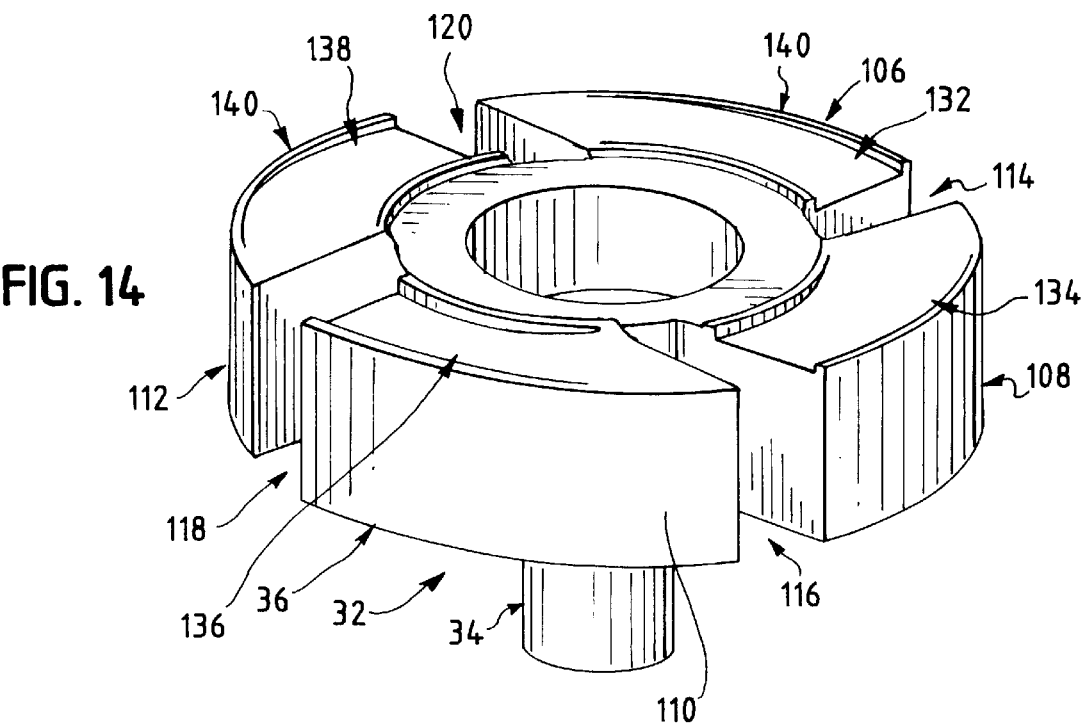
FIG. 14 is a front, perspective view of a rotor having a shaft and an impeller.
Figure 15:
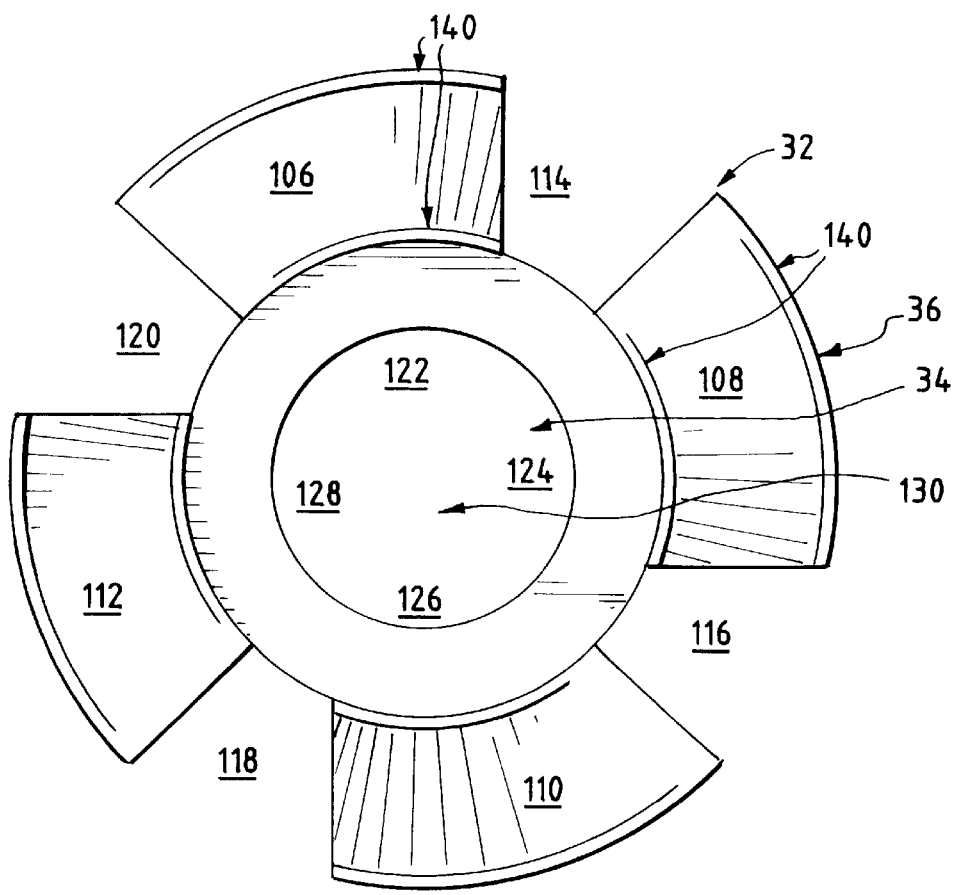
FIG. 15 is an end view of a rotor having a shaft and an impeller.
Figure 16:
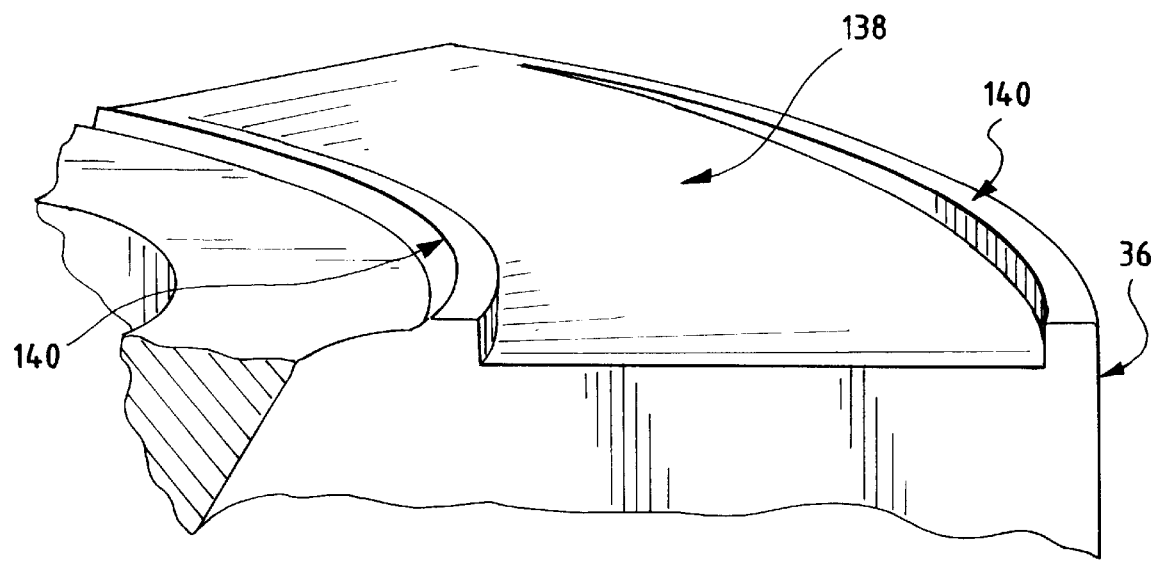
FIG. 16 is an enlarged fragmentary view of the end of the impeller.

FIGS. 14, 15 and 16 provide details of preferred embodiments of the rotor 32 including the shaft 34 and the impeller 36 in order to show features which are incorporated to ensure effective movement of blood. In this particular embodiment, the impeller 36 has four blade sectors 106, 108, 110 and 112. The blade sectors 106, 108, 110 and 112 are separated by slots 114, 116, 118 and 120. As best shown in FIG. 15, the shaft 34 includes flow passages 122, 124, 126 and 128. In addition, a fluid-drive channel 130 is provided in shaft 34. The slots 122, 124, 126, 128 and the channel 130 are designed in order to keep blood from stagnating and clotting in areas near and around the shaft 34. In the shaftless embodiments, these features would not be present and there would be a straight circular bore through the center of the impeller.

The impeller 36 includes, on the faces of its blades defining the hydrodynamic thrust bearing, tapered surfaces 132, 134, 136 and 138 in the end of each blade 106, 108, 110 and 112. The tapered surfaces 132, 134, 136 and 138 are of maximum depth at leading edges of the blades and gradually decrease in depth. These tapered surfaces 132, 134, 136 and 138 are designed to ensure blood moves through the gap 88 in and feed the hydrodynamic thrust bearing created in this gap 88. At the periphery of the tapered surfaces 132, 134, 136 and 138, the impeller 36 is provided with shrouds or end walls 140 to channel blood into and through the hydrodynamic thrust bearings.

Various specific combinations of hydrodynamic, magnetic and hybrid hydrodynamic/magnetic bearings have been described. It is contemplated that other combinations would be useful and should be considered to be within the scope of the invention.

Although illustrative embodiments of the invention have been shown and described, it is to be understood that various modifications and substitutions may be made by those skilled in the art without departing from the novel spirit and scope of the present invention.

What is claimed is:

1. A rotary blood pump comprising:

a pump housing;

a rotor within said housing and comprising an impeller;

at least one hydrodynamic thrust bearing defined by a gap between the impeller and the housing; and at least one hydrodynamic radial bearing defined by a gap between the impeller and an extension of said housing extending towards the impeller wherein said gap between said impeller and said inward extension of said housing has a greater clearance than a clearance of said gap between said impeller and said housing of said hydrodynamic thrust bearing.

2. The rotary blood pump of claim 1 wherein the the gap defining the hydrodynamic thrust bearing has a minimum clearance of about 0.0005–0.0015 inches.

3. The rotary blood pump of claim 2 wherein the gap defining the radial bearing has a minimum clearance of about 0.006–0.020 inches.

4. The rotary blood pump of claim 1 further comprising one or more magnets and one or more motor stators which are offset with respect to each other.

5. A rotary blood pump comprising:

a pump housing;

a rotor within said housing and comprising an impeller;

at least one hydrodynamic thrust bearing defined by a gap between the impeller and the housing; and wherein an inside face of the housing and a portion of a rear face of the impeller comprise complementary shaped surfaces defining a gap with sufficient clearance such that said gap does not provide radial hydrodynamic support.

6. The rotary blood pump of claim 5 wherein the gap defining the hydrodynamic thrust bearing has a minimum clearance of about 0.0005–0.0015 inches.

7. The rotary blood pump of claim 5 wherein the gap defining said complementary surfaces has a minimum clearance of about 0.006–0.020 inches.

8. The rotary blood pump of claim 5 wherein the gap defining said complementary surfaces has a minimum clearance of at least about 0.010 inch.

9. The rotary blood pump claim 5 further comprising one or more magnets and one or more stators which are offset with respect to each other.

10. A rotary blood pump comprising:
   a pump housing;
   a rotor within said housing and comprising an impeller
   at least one hydrodynamic thrust bearing defined by a gap between the impeller and the housing; and
   at least one hydrodynamic radial bearing defined by a gap between the impeller and an inward extension of said housing, wherein radial support of said impeller is provided solely by said hydrodynamic radial bearing.

11. The rotary blood pump of claim 10 wherein the gap defining the hydrodynamic thrust bearing has a minimum clearance of about 0.0005–0.0015 inches.

12. The rotary blood pump of claim 10 wherein the gap defining the hydrodynamic radial bearing has a minimum clearance of about 0.0005–0.0015 inches.

13. The rotary blood pump of claim 10 further comprising one or more magnets and one or more motor stators which are offset with respect to each other.

14. A shaftless rotary blood pump comprising:
   a pump housing;
   a shaftless rotor comprising an impeller;
   at least one magnetic radial bearing comprising one or more magnets carried by said impeller and one or more magnets carried by an inward extension of said housing; and
   at least one hydrodynamic thrust bearing defined by a gap between the impeller and the housing.

15. The shaftless rotary blood pump of claim 14 wherein the gap defining said magnetic radial bearing has a minimum clearance of about 0.003 inch.

16. The shaftless rotary blood pump of claim 14 wherein the gap defining said magnetic radial bearing has a minimum clearance of about 0.006–0.020 inches.

17. The shaftless rotary blood pump of claim 14 wherein the gap defining said hydrodynamic thrust bearing has a minimum clearance of about 0.0005–0.0015 inches.

18. The shaftless rotary blood pump of claim 14 further comprising one or more magnets and one or more motor stators which are offset with respect to each other.

19. A shaftless rotary blood pump comprising:
   a pump housing;
   a shaftless rotor comprising an impeller;
   at least one hydrodynamic, magnetic radial bearing comprising one or more magnets carried by said impeller and one or more magnets carried by an inward extension of said housing; and
   at least one hydrodynamic thrust bearing defined by a gap between the impeller and the housing.

20. The shaftless rotary blood pump of claim 19 wherein the gap defining said hydrodynamic, magnetic radial bearing has a minimum clearance of about 0.002–0.008 inches.

21. The shaftless rotary blood pump of claim 19 wherein the gap defining said hydrodynamic thrust bearing has a minimum clearance of about 0.0005–0.0015 inches.

22. The shaftless rotary blood pump of claim 19 further comprising one or more magnets and one or more motor stators which are offset with respect to each other.

23. A shaftless rotary blood pump comprising;
   a pump housing;
   a shaftless rotor comprising an impeller;
   at least two magnetic radial bearings each comprising one or more magnets carried by said impeller and one or more magnets carried by an inward extension of said housing; and
   at least one hydrodynamic thrust bearing defined by a gap between the impeller and the housing.

24. The shaftless rotary blood pump of claim 23 wherein the gap defining said magnetic radial bearings has a minimum clearance of about 0.010 inch.

25. The shaftless rotary, blood pump of claim 24 wherein the gap defining said hydrodynamic thrust bearing has a minimum about 0.0005–0.0015 inches.

26. The shaftless rotary blood pump of claim 23 further comprising one or more magnets and one or more motor stators which are offset with respect to each other.

* * * * *